US006036972A

United States Patent [19]

Nakamura et al.

[11] Patent Number: 6,036,972

[45] **Date of Patent: *Mar. 14, 2000**

[54] METHOD OF TREATING DILATED CARDIOMYOPATHY

[76] Inventors: Toshikazu Nakamura, 4-1, Takamidai, Takatsuki-shi, Osaka 569; Kazuo Komamura, 2-15-5, Kitayamato, Ikoma-shi, Nara 630-01; Kunio Miyatake, 2-8-3, Aoshinke, Minoo-shi, Osaka 562, all of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/949,864

[22] Filed: Oct. 14, 1997

[30] Foreign Application Priority Data

Apr. 14, 1997 [JP] Japan .................................... 6-113360

[51] Int. Cl.[7] ........................... A61K 38/00; A61K 38/18

[52] U.S. Cl. .................................. 424/422; 514/2; 514/8; 514/21; 530/350; 530/399

[58] Field of Search ..................... 514/2, 8, 21; 530/350, 530/399; 424/422

[56] References Cited

U.S. PATENT DOCUMENTS 5,652,225 7/1997 Isner .......................................... 514/44

OTHER PUBLICATIONS

"Abstracts From the 69th Scientific Sessions," American Heart Association, Nov. 10–13, 1996.

Japanese Circulation Journal, vol. 61 p. 472 (Mar. 5, 1997).

*Primary Examiner*—Thurman K. Page
*Assistant Examiner*—Lakshmi Channavajjala
*Attorney, Agent, or Firm*—Birch, Stewart, Kolasch & Birch, LLP

[57] ABSTRACT

The invention describes to a method of treating a patient with dilated cardiomyopathy comprising administering an effective amount of Hepatocyte Growth Factor (HGF).

11 Claims, 4 Drawing Sheets

METHOD OF TREATING DILATED CARDIOMYOPATHY

BRIEF SUMMARY OF THE INVENTION

The present invention relates to a method of treating a patient of dilated cardiomyopathy comprising administering an effective amount of Hepatocyte Growth Factor (HGF).

BACKGROUND OF THE INVENTION

Figure 1:
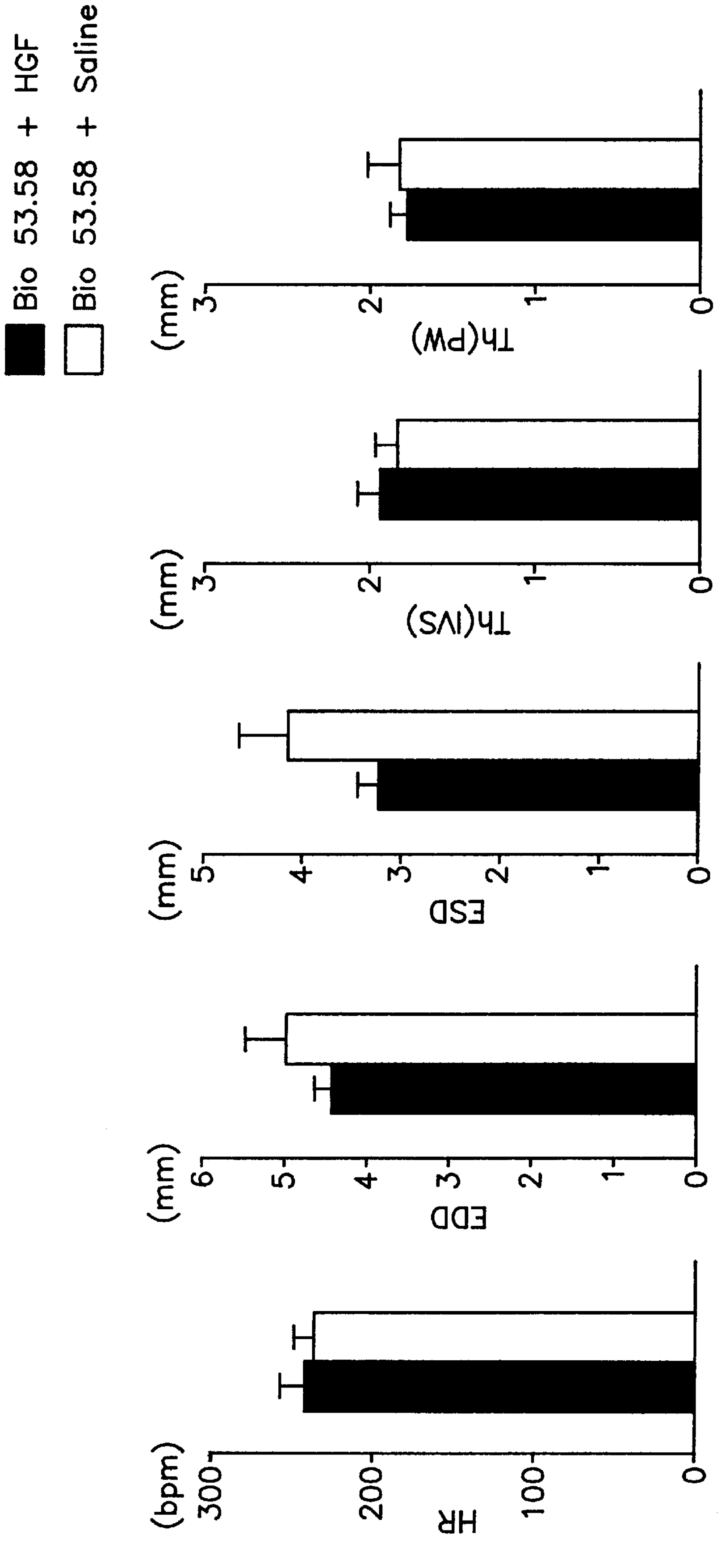
FIG. 1 Comparison of heart rates, volume of left ventricular (end-diastolic dimension EDD, end-stolic dimension ESD), and wall thickness (inter ventricular septum Th(IVS), posterior wall Th(PW)).
Figure 2:
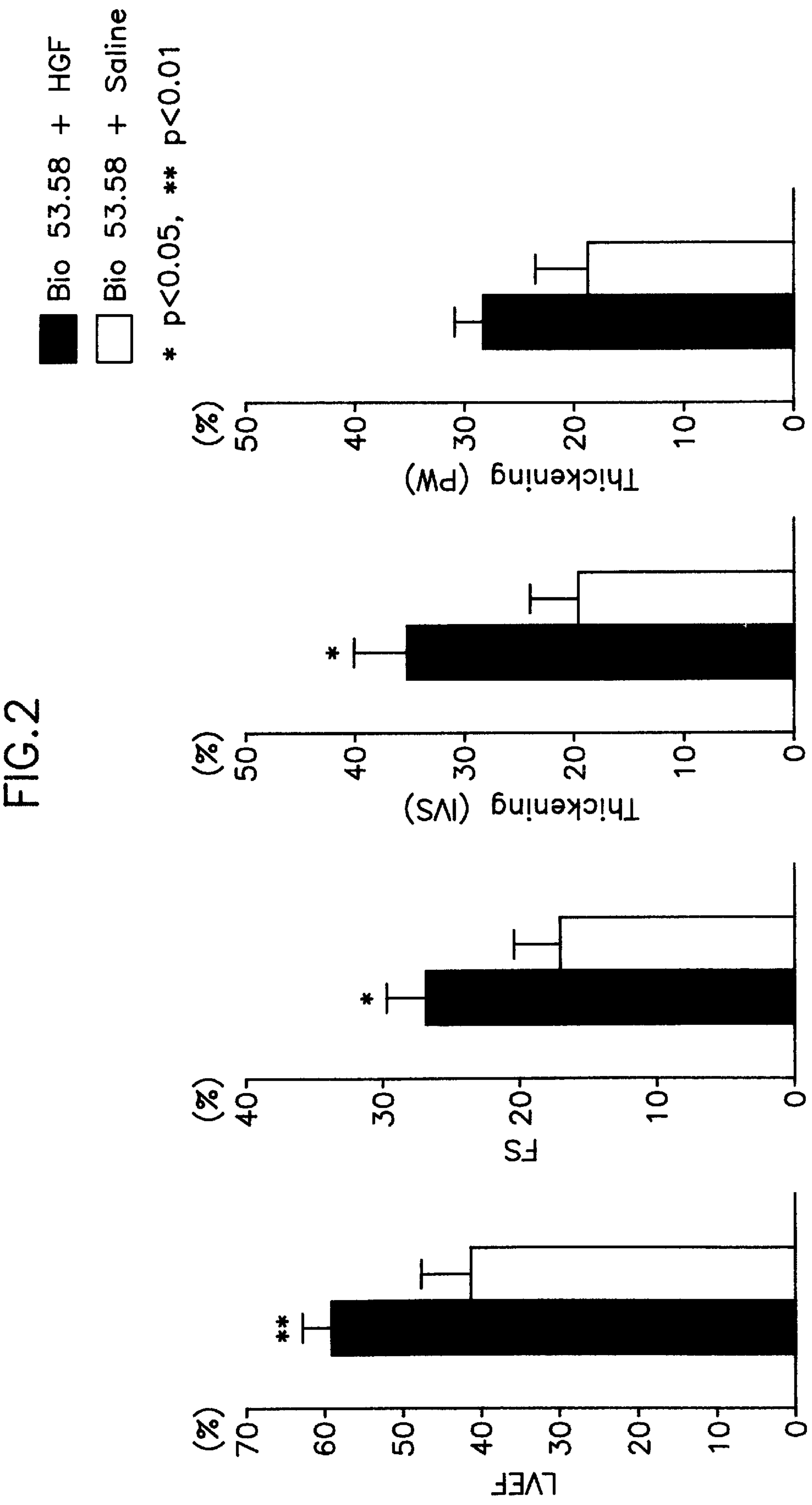
FIG. 2 Comparison of left ventricular ejection fraction (LVEF), left ventricular fractional shortening (FS), and wall thickening (interventricular septum IVS).
Figure 3:
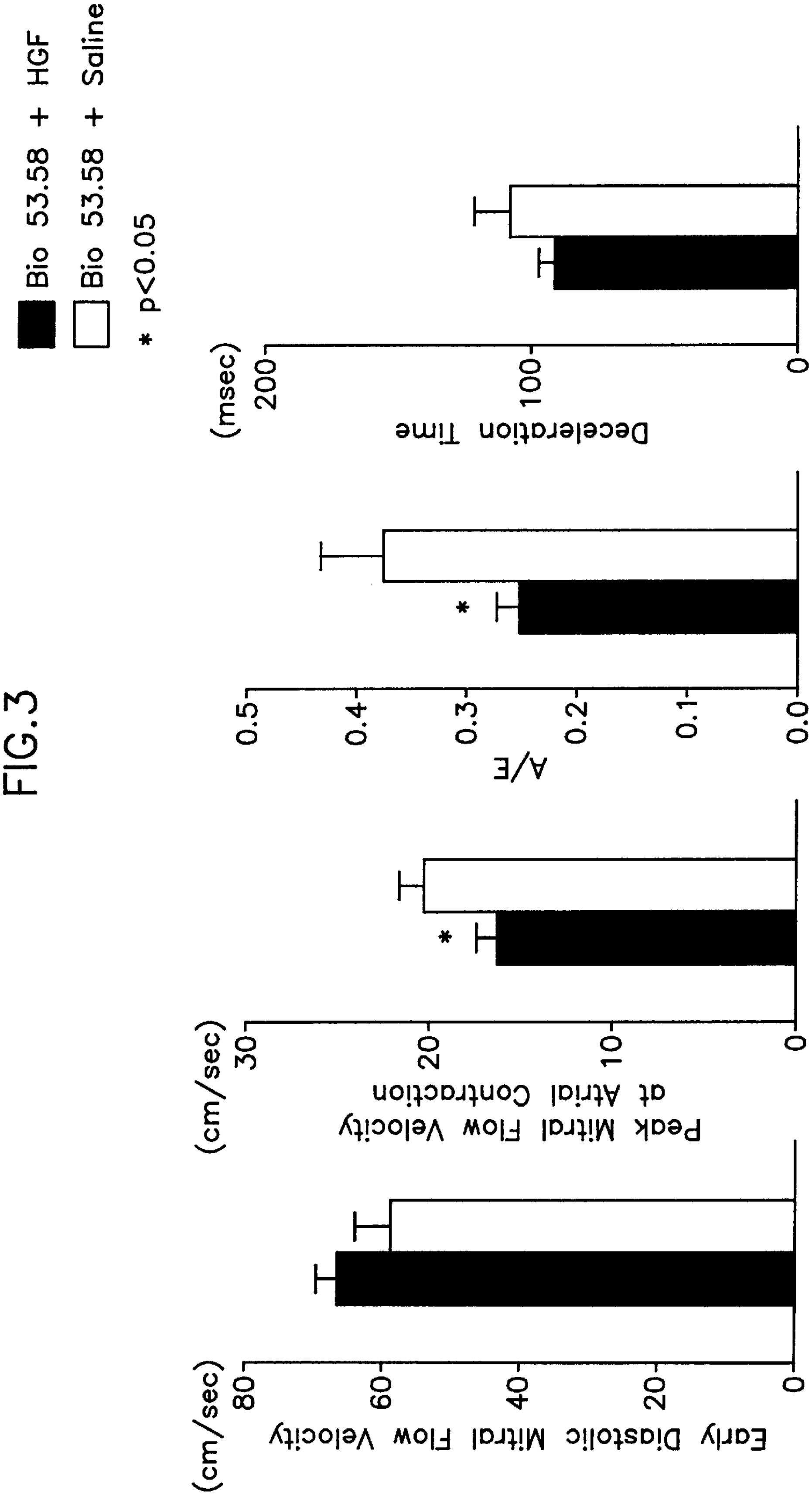
FIG. 3 Comparison of early diastolic mitral flow velocity, deceleration time of early diastolic mitral flow velocity, peak mitral flow velocity at atrial contraction and A/E (ratio of early diastolic mitral flow velocity to peak mitral flow velocity at atrial contraction).
Figure 4:
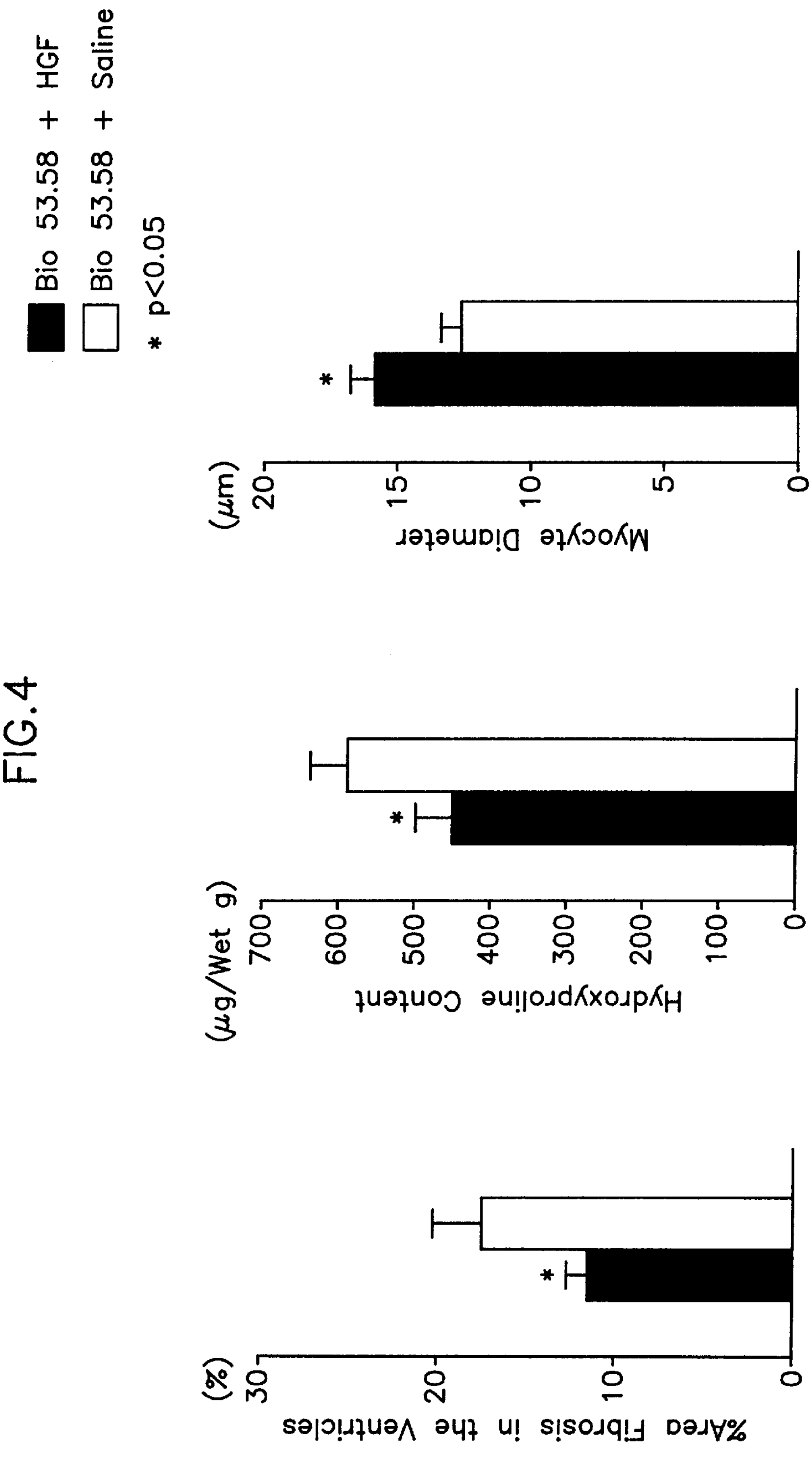
FIG. 4 Comparison of the percentage area fibrosis (i.e. aniline blue-positive area) in She ventricles, the hydroxyproline content and myocyte diameter.

One of the critical symptoms of patients with dilated cardiomyopathy is a reduction of ventricular performance, resulting in an expansion of the left ventricle. The patients often have reduction in left ventricular cardiac output, increase in left ventricular diastolic pressure, and congestive heart failure. Since not all patients with dilated cardiomyopathy have congestive heart failure, the name of dilated cardiomyopathy is more practical than the name of congestive cardiomyopathy in this meaning. The symptom is acute or latent and the patients are likely to have intractable heart failure in the terminal stage.

Pathologically, dilated cardiomyopathy is accompanied with diffuse or local degeneration, fibrosis and atrophy of cardiac myocardium, and the rest of cardiac myocytes is frequently found to be hypertrophied. Dilated cardiomyopathy is thought to be caused by the taking of excess alcohol, virus infection, spasm of microvessels, disorder of immunity and so on, however the real cause has not been clearly understood. Since some dilated cardiomyopathy may occur in a pedigree, it is suggested that a genetic background might be involved. Dilated cardiomyopathy may cause heart failure, lethal arrhythmia or thromboembolism, and its prognosis is poor. Ischemic cardiomyopathy may cause heart failure, and hypertensive heart diseases. In treatment of dilated cardiomyopathy, it is not enough to control an each factor independently but is necessary to control several factors simultaneously.

A quarter of patients of heart failure have dilated cardiomyopathy, and about a half of patients of dilated cardiomyopathy need heart transplantation. Recently the causes of dilated cardiomyopathy have been made clearer. In the definition of dilated cardiomyopathy by the Committee of WHO/ISFC, it is described that the causes are genetic heredity, virus infection, alcohol and so on.

In cardiac myocytes, chronic inflammation caused by virus infection or disorder of immunity can activate many transcriptional factors simultaneously, resulting in continuous production of autoantibodies, expression of MHC and adhesion molecules, production of cytokines, and the activation of oncogenes. The disorder of immunity through MHC and the mutation of genes can also damage cardiac cells. These continuous damages to cardiac myocytes may develop into some kind of cardiomyopathy, but the mechanism has not been clear.

Typical symptoms of dilated cardiomyopathy are pulmonary congestion and reduction of ventricular cardiac output caused by left heart left failure. The patients with dilated cardiomyopathy have limitation of movement because of dyspnea and fatigue. Concomitant failure of the right heart provokes peripheral edema. An important aim of the treatment is not only amelioration of the symptoms by improvement of circulation, but also to prolong their life span, since dilated cardiomyopathy is progressive and has a poor prognosis. It seems quite difficult to cure the disease completely, but recently accelerating factors or inhibiting factors of cardiomyopathy have been studied and reported, and a medicine that can control the progress and prolong life has been developed. Activation of sympathetic nerves and reninangiotensin-aldosterone system are important factors for deterioration of cardiomyopathy. Inhibition of these factors will not only reduce the progress of heart failure, but also to improve some symptoms of cardiomyopathy, resulting in improving heart failure. It is also important to modify patients' life styles to improve symptoms and to prevent the exacerbation of heart failure. It is also necessary to prevent or treat infection, anemia, disorder of thyroid function and so on, as soon as possible. Diabetes mellitus, excess of alcohol, long lasting tachycardia can cause cardiomyopathy similar to dilated cardiomyopathy. Dilated cardiomyopathy does not accompany a specific disease, but accompanies arrhythmia and thromboembolism that will be crucial to death.

Since the survival rate of dilated cardiomyopathy for five years is from 50 to 60% and its prognosis is poor, the cause of the disease is expected to be revealed and a method of treatment is also eagerly sought to be developed.

Hepatocyte Growth Factor (HGF) is a protein and is found as a factor for promoting growth of hepatocyte in vitro (Biochem. Biophys. Res. Commun., 122, 1450, 1984, Proc. Natl. Acad. Sci. USA, 83, 6489, 1986, FEBS Letter, 22, 311, 1987, Nature, 342, 440, 1989, Proc. Natl. Acad. Sci. USA, 87, 3200, 1990). HGF that is found as a growth factor specific to hepatocyte is revealed to have activities such as healing damaged tissues in vivo in recent studies. HGF is not only a material for research, but also is expected to be developed as a medicine for human, a mammal, or an animal.

HGF is revealed to be mainly produced from mesenchymal, and is provided to neighboring cells by paracrine. HGF has an activity of healing a damaged tissue through the paracrine mechanism. Since non-damaged organs such as a lung shows increased production of HGF, when liver or kidney is damaged or injured, HGF is considered to be provided through endcrine mechanism as well.

In recent studies relating to HGF receptors it is revealed that c-Met protooncogene codes HGF receptor (Bottaro et al., Science 251, 802–804, 1991, Naldini et al., Oncogene 6, 501–504, 1991).

As described above, HGF has many activities, but it is not known that HGF is effective in treatment, or improvement of symptoms of dilated cardiomyopathy.

DETAILED DESCRIPTION OF THE INVENTION

Present invention provides a method of treating a patient of dilated cardiomyopathy comprising administering an effective amount of HGF. The present invention also provides a method of treating a mammal such as human, bovine, horse, pig, sheep, dog, cat with dilated cardiomyopathy comprising administering an effective amount of HGF.

The present inventors show in an example described below that HGF has an activity of treatment, or improvement of symptoms to a hamster Bio 53.58, which is an animal model of spontaneous dilated cardiomyopathy. Since HGF does not show any activity to a non-damaged organ or a tissue and shows an activity only to a damaged or an injured organ or tissue, these facts show that HGF does not have serious side effects. The present invention also provides a safe and efficient method of treating a patient with dilated cardiomyopathy comprising administering an effective amount of HGF.

In the present invention, HGF prepared by various methods can be used.

The methods of preparing HGF are well known to a person skilled in the art. For example, HGF may be prepared by a process comprising the steps of; extracting from an organ such as a liver, spleen, a lung, bone marrow, brain, kidney, placenta, blood cells such as platelets, white blood cells, plasma, serum and the like of a mammal such as a rat, bovine, horse, sheep and the like; and purifying the extraction (FEBS Letters, 224, 312, 1987, Proc. Natl. Acad. Sci. USA, 86, 5844, 1989).

HGF may also be prepared by a process which comprises the steps of;

culturing primary cells or a cell line which produce(s) HGF; extracting from the cultured product (supernatant fluid, cultured cells, etc); and purifying HGF from the extract.

HGF may be prepared by genetic engineering method comprising the steps of;

inserting a gene encoding HGF to an appropriate vector; transfecting a host cell by inserting said inserted vector; and purifying HGF from the supernatant of the cultured transfected cells (for example Nature, 342, 440, 1989; Japanese patent application KOKAI 5-111383; Japanese patent application KOKAI 3-255096; Biochem. Biophys. Res. Commun., 163, 967, 1989).

Said host cell is not limited, and various host cells conventionally used in genetic engineering methods can be used, which are, for example, *Escherichia coli, Bacillus subtilis,* yeast, mold fungi, plant and animal cells and the like.

A more specific process of preparing HGF from a living tissue comprises the steps of;

administering carbon tetrachloride to a rat intraperitoneally to make said rat hepatitis;

removing a liver from said rat and homogenizing; and purifying by a conventional method of a protein purification such as gel column chromatography (such as S-Sepharose, heparinsepharose and the like), HPLC and the like.

HGF may be prepared by a genetic engineering process comprising the steps of;

transforming an animal cell (such Chinese Hamster Ovary (CHO) cells, mouse C127 cells, monkey COS cells, Sf (*Spodoptera frugiperda*) cells and the like) with a gene encoding amino acid sequence of HGF; and purifying from the supernatant fluid of said cells.

HGF includes human HGF and mammalian HGF, preferred HGF is a human HGF, and more preferred HGF is a human recombinant HGF (Japanese patent application KOKAI 5-111383 (1993)).

A HGF prepared by the above processes includes any HGF that has substantially the same activities such as a partial deletion derivative of the amino acid sequence, a substitution derivative of an amino acid, an insertion derivative of other amino acid sequence, a derivative from binding one or more amino acids to N- or C- terminus of the amino acid sequence, or a sugar chain deletion or substitution derivatives.

HGF may be formulated in various ways such as liquid preparations, solid preparations, capsule preparations, depot preparations and the like. HGF may be formulated for parenteral administration for injection without any carrier or with an appropriate conventional carrier and for oral administration with an appropriate conventional carrier. The formulation for parenteral administration for injection may be prepared by conventional methods known to a person skilled in the art, such as a method comprising the steps of; dissolving HGF in an appropriate solvent such as sterilized water, buffered solution, isotonic sodium chloride solution and the like; sterilizing by filtration; and filling said solution to a sterilized bottle. An amount of HGF in the parenteral formulation is from about 0.0002 to about 0.2 (W/V %), and preferred amount is from about 0.001 to about 0.1 (W/V %). The formulation may be prepared by the conventional formulation technique. The amount of HGF may be varied depending on a formulation, a disease and the like.

HGF may be formulated in rectal compositions such as suppositories or retention enemas, e.g. containing conventional suppository bases such as cocoa butter water soluble bases (glycerinated gelatin, macrogols, etc.) or other glyceride.

HGF may be administered in the form of inhalation or insufflation. For administration by inhalation or insufflation HGF in conveniently delivered in the form of an aerosol spray presentation from pressurised packs or nebulizer, with the use of suitable propellants such as carbon dioxide or other suitable gasses.

HGF may be administered using conventional drug delivery systems well known to a person skilled in the art. Examples of the preparations for drug delivery system are microspheres (nanoparticle, microparticle, microcupsule, bead, liposome, multiple emulsion, etc.) and the like.

Preferably a stabilizer may be added to the formulation, and the examples of a stabilizer include albumin, globulin, gelatin, mannitol, glucose, dextran, ethylene glycol and the like. The formulation of the present invention may include a necessary additive such as an excipient, a solubilizer, an antioxidant agent, a pain-alleviating agent, an isotonic agent and the like. The liquid formulation may be stored in frozen condition, or after removal of water by a process such as freeze-drying. The freeze-dried preparations are used by dissolving in pure water for injection and the like before use.

Effective dosages and schedules for administering HGF may be determined empirically, and such determinations are within the skill in the art. An administration route of the preparation may vary depending on the form of preparation. For example, the parenteral preparation may be administered intravenously, intraarterially, subcutaneously or intramuscularly. The amount of administration may vary depending on a symptom, an age, and a weight, etc. of a patient. A dose can be selected from the range of from 0.1 $\mu$g to 10 mg/kg. The preparation of HGF may be administered once or several times per day.

HGF may also be formulated as depot preparations. Such long acting formulations may be administered by implantation (for example subcutaneously or intramuscularly) or intramuscular injection. Thus, for example, HGF may be formulated with suitable polymeric or hydrophobic materials (for example as an emulsion in an acceptable oil) or ion exchange resins or as sparing soluble derivatives, for example as a sparingly soluble salt.

Effective dosages and schedules for administering the depot preparation may be determined empirically, and such determinations are within the skill in the art. An administration route of the depot preparation may vary depending on the form of preparation.

The preferred administration of the depot preparations is once a day for at least one week, preferably once a day for at least one month, more preferably once a day at least three months.

EXAMPLES

The following examples are for illustrative purposes only and are not to be construed as limiting the invention.

Example 1

Cardiomyopathic Hamster Bio 53.58

HGF (450 $\mu$g/Kg) was administered intraperitoneally once a day for 30 days to cardiomyopathic hamster Bio 53.58 (Group A, 3 month-old, n=10). Saline was also administered intraperitoneally once a day for 30 days to control cardiomyopathic hamster Bio 53.58 (Group B, 3 month-old, n=8).

Cardiac dimension was measured by a cardiac Doppler and echocardiography. There are no significant differences in heart rates, volume of left ventricle (end-diastolic dimension EDD, end-systolic dimension EDD), wall thickness (ventricular septum) between the group A and group B.

As to systolic function, left ventricular ejection fraction (LVEF), left ventricular fractional shortening (FS), wall thickening (interventricular septum IVS) were significantly improved in the group A as compared to the group B.

As to diastolic function, early diastolic mitral flow velocity and deceleration time of early diastolic mitral flow velocity were similar between the two groups. However, peak mitral flow velocity at atrial contraction and A/E (ratio of early diastolic mitral flow velocity to peak mitral flow velocity at atrial contraction) were greater ($p<0.05$) in the group B than in the group A.

Heart weight and left ventricular weight were similar between the two groups.

Histopathological analysis revealed that the percent area of fibrosis (i.e. aniline blue-positive area) in the ventricles and the hydroxyproline content were reduced in the group A. In addition, larger myocyte diameter and the reduction of vacuolization and nuclear dysplasia were observed in the group A. Calcium deposition and infiltration of inflammatory cells to myocardium were decreased in the group A.

The data revealed that HGF is effective to cardiomyopathic hamster Bio 53.58.

Example 2

To a saline solution (100 ml) is added HGF (1 mg), mannitol (1 g) and polysolvate 80 10 mg sterilely. The solution was divided to 1 ml and charged into vial. Freeze-dry preparation was obtained after freeze-drying and sealing.

Example 3

To a phosphate buffer solution containing 0.15M NaCl and 0.01% polysolvate (100 ml) is added HGF (1 mg) and human serum albumin (100 mg) sterilely. The solution was divided to 1 ml and charged into vial. Freeze-dry preparation was obtained after freeze-drying and sealing.

What is claimed is:

1. A method of treating a patient with dilated cardiomyopathy comprising administering an effective amount of hepatocyte growth factor.

2. A method of treating a mammal with dilated cardiomyopathy comprising administering an effective amount of hepatocyte growth factor.

3. The method of claim 1, wherein hepatocyte growth factor is administered as a formulation selected from the group consisting of a liquid preparation, solid preparation, capsule preparation, and depot preparation.

4. The method of claim 1, wherein said hepatocyte growth factor is administered as a formulation selected for parenteral administration.

5. The method of claim 1, wherein said formulation further comprises a pharmaceutically acceptable carrier.

6. The method of claim 4, wherein said formulation further comprises at least one of a stabilizer, excipient, solubilizer, antioxidant, pain-alleviating agent, and an isotonic agent.

7. The method of claim 5, wherein said formulation further comprises at least one of a stabilizer, excipient, solubilizer, antioxidant, pain-alleviating agent, and an isotonic agent.

8. The method of claim 5 wherein said parenteral administration is administered intravenously, interarterially, subcutaneously, or intramuscularly.

9. The method of claim 1, wherein said hepatocyte growth factor is administered in a dose of from 0.1 $\mu$g/kg to 10 mg/kg.

10. The method of claim 2, wherein said hepatocyte growth factor is administered as a formulation selected for parenteral administration.

11. The method of claim 2, wherein said hepatocyte growth factor is administered in a dose of from 0.1 $\mu$g/kg to 10 mg/kg.

* * * * *